(12) United States Patent
Hsu

(10) Patent No.: US 12,419,864 B2
(45) Date of Patent: Sep. 23, 2025

(54) METHOD FOR TREATING CANCERS

(71) Applicant: Acura Nanomedicine Corporation, New Taipei (TW)

(72) Inventor: Hung-Kun Hsu, New Taipei (TW)

(73) Assignee: Acura Nanomedicine Corporation, New Taipei (TW)

( * ) Notice: Subject to any disclaimer, the term of this patent is extended or adjusted under 35 U.S.C. 154(b) by 694 days.

(21) Appl. No.: 17/770,289

(22) PCT Filed: Oct. 20, 2020

(86) PCT No.: PCT/CN2020/122269
§ 371 (c)(1),
(2) Date: Apr. 20, 2022

(87) PCT Pub. No.: WO2021/078126
PCT Pub. Date: Apr. 29, 2021

(65) Prior Publication Data
US 2022/0387391 A1 Dec. 8, 2022

Related U.S. Application Data

(60) Provisional application No. 62/923,631, filed on Oct. 21, 2019, provisional application No. 62/923,629, filed on Oct. 21, 2019.

(51) Int. Cl.
*A61K 31/4168* (2006.01)
*A61K 31/4706* (2006.01)
*A61P 35/00* (2006.01)

(52) U.S. Cl.
CPC ...... *A61K 31/4168* (2013.01); *A61K 31/4706* (2013.01); *A61P 35/00* (2018.01)

(58) Field of Classification Search
CPC .. A61K 31/4168; A61K 31/4706; A61P 35/00
See application file for complete search history.

(56) References Cited

PUBLICATIONS

Sung, So Jung, et al. "Autophagy is a potential target for enhancing the anti-angiogenic effect of mebendazole in endothelial cells." Biomolecules & therapeutics 27.1 (2019): 117. (Year: 2019).*

(Continued)

*Primary Examiner* — James H Alstrum-Acevedo
*Assistant Examiner* — Justin Christopher Sanchez
(74) *Attorney, Agent, or Firm* — NZ Carr Law Office

(57) ABSTRACT

Provided herein are methods and formulations for reducing viability of a cancer or enhancing susceptibility of a cancer to an anti-cancer agent. The method includes administering to the subject an effective amount of an anti-parasitic agent and an autophagy inhibitor to the subject. Additionally or optionally, the method further includes administering to the subject the anti-cancer agent. Also provided herein are formulations for the treatment of cancers, particularly cancers that are unresponsive to anti-cancer agents. The formulation includes at least two agents selected from the group consisting of an anti-parasitic agent, an autophagy inhibitor and an HDAC inhibitor; and a pharmaceutically acceptable excipient.

6 Claims, 13 Drawing Sheets

(56) References Cited

PUBLICATIONS

Balic, Anamaria, et al. "Chloroquine targets pancreatic cancer stem cells via inhibition of CXCR4 and hedgehog signaling." Molecular cancer therapeutics 13.7 (2014): 1758-1771. (Year: 2014).*
Ammerpohl, O., et al. "Complementary effects of HDAC inhibitor 4-PB on gap junction communication and cellular export mechanisms support restoration of chemosensitivity of PDAC cells." British journal of cancer 96.1 (2007): 73-81. (Year: 2007).*

* cited by examiner

METHOD FOR TREATING CANCERS

CROSS-REFERENCE TO RELATED APPLICATION

This application is a U.S. National Stage Filing under 35 U.S.C. 371 from International Patent Application Serial No. PCT/CN2020/122269, entitled "METHODS FOR TREATING CANCERS" filed Oct. 20, 2020, and published on Apr. 29, 2021, which claims the priority to U.S. Provisional Application Nos. 62/923,629 and 62/923,631 filed Oct. 21, 2019, the disclosure of which are incorporated by reference herein in their entireties.

BACKGROUND OF THE INVENTION

1. Field of the Invention

The present disclosure relates to treatment of cancers. More particularly, to treatment of cancers unresponsive or resistant to anti-cancer agent (e.g., chemotherapeutic agent).

2. Description of Related Art

Cancer therapy is often hampered by the rapid emergence of drug resistance, especially for drugs in the conventional chemotherapy category. For example, for the treatment of pancreatic cancer, less than 20% of pancreatic cancers are amenable to surgery; as to invasive and metastatic pancreatic cancers, they respond poorly to existing treatments in chemotherapy and radiotherapy. Thus, the overall survival rate is less than 4% and the median survival time after diagnosis is less than a year. This lack of overall survival benefit is the consequence of the rapid emergence of drug resistant variants, that is, gemcitabine resistant cancerous cells.

In view of the above, there exists in the related art a need of an improved way of combating the drug resistance issue in cancer therapy.

SUMMARY

This invention is based on the unexpected discovery that certain agents may reduce the viability of cancerous cells or enhance susceptibility of cancer cells, particularly, drug resistant cancer cells, toward an anti-cancer agent.

Accordingly, the first aspect of the present disclosure is directed to a method for treating a cancer in a subject. The method includes administering to the subject an effective amount of an anti-parasitic agent and an autophagy inhibitor so as to reduce the viability of the cancer Examples of the anti-parasitic agent suitable for use in the present method include, but are not limited to, albendazole, amphotericin B, benzimidazole, diethylcarbamazine, eflornithine, febantel, fenbendazole, flubendazole, fumagillin, lvermectin, mebendazole (MBZ), melarsopol, metronidazole, miltefosine, netobimin, niclosamide, nitazoxanide, oxfendazole, oxifendazole, oxibendazole, praziquantel, pyrantel pamoate, rifampin, thiabendazole, thiophanate, tinidazole, and triclabendazole.

Examples of the autophagy inhibitor suitable for use in the present method include, but are not limited to, bafilomycin A1, bortezomib, chloroquine (CQ), hydroxychloroquine (HCQ), 3-methyladenine (3-MA) and quinacrine.

According to embodiments of the present disclosure, the cancer treatable by the present method may be bladder cancer, breast cancer, brain tumor, colon cancer, head and neck cancer, leukemia, lung cancer, liver cancer, lymphoma, kidney cancer, melanoma, neuroepithelioma, ovarian cancer, pancreatic cancer, prostate cancer, rectal cancer, stomach cancer, or uterus cancer. In some embodiments, the cancer treatable by the present method is pancreatic cancer. In other embodiments, the cancer treatable by the present method is liver cancer. In further embodiments, the cancer treatable by the present method is brain tumor.

According to embodiments of the present disclosure, the cancer treatable by the present method may be resistant to an anti-cancer agent, such as gemcitabine, doxorubicin, sorafenib, and temozolomide (TMZ). In some embodiments, the cancer treatable by the present method is resistant to gemcitabine. In other embodiments, the cancer treatable by the present method is resistant to sorafenib.

According to some embodiments of the present disclosure, the subject has the pancreatic cancer, and the viability of the cancer is suppressed by the combined treatment of MBZ and CQ, or the combined treatment of MBZ and HCQ.

According to other embodiments of the present disclosure, the subject has the gemcitabine resistant pancreatic cancer, and the viability of the cancer is suppressed by the combined treatment of MBZ and CQ, or the combined treatment of MBZ and HCQ.

According to further embodiments of the present disclosure, the subject has the liver cancer, and the viability of the cancer is suppressed by the combined treatment of MBZ and CQ, or the combined treatment of MBZ and HCQ.

According to further embodiments of the present disclosure, the subject has the brain cancer, and the viability of the cancer is suppressed by the combined treatment of MBZ and CQ, or the combined treatment of MBZ and HCQ.

The second aspect of the present disclosure is directed to a method of enhancing susceptibility of a cancer in a subject to an anti-cancer agent. The method comprises administering to the subject an effective amount of a sensitizer before, during or after the administration of the anti-cancer agent, in which the sensitizer comprises at least two agents selected from the group consisting of an anti-parasitic agent, an autophagy inhibitor, and a histone deacetylase (HDAC) inhibitor.

According to embodiments of the present disclosure, the anti-cancer agent is selected from the group consisting of gemcitabine, doxorubicin, sorafenib, and TMZ.

According to embodiments of the present disclosure, the anti-parasitic agent suitable for use in the present method may be any of albendazole, amphotericin B, benzimidazole, diethylcarbamazine, eflornithine, febantel, flubendazole, fenbendazole, fumagillin, lvermectin, mebendazole (MBZ), melarsopol, metronidazole, miltefosine, netobimin, niclosamide, nitazoxanide, oxfendazole, oxifendazole, oxibendazole, praziquantel, pyrantel pamoate, rifampin, thiabendazole, thiophanate, tinidazole, and triclabendazole.

According to embodiments of the present disclosure, the autophagy inhibitor suitable for use in the present method may be bafilomycin A1, bortezomib, CQ, HCQ, 3-MA or quinacrine.

According to embodiments of the present disclosure, the HDAC inhibitor suitable for use in the present method may be any of belinostat, 4-phenylbutyrate (4-PB), romidepsin, or vorinostat.

According to embodiments of the present disclosure, the cancer treatable by the present method may be bladder cancer, breast cancer, brain tumor, colon cancer, head and neck cancer, leukemia, lung cancer, liver cancer, lymphoma, kidney cancer, melanoma, neuroepithelioma, ovarian cancer, pancreatic cancer, prostate cancer, rectal cancer, stomach cancer, or uterus cancer. In some embodiments, the cancer treatable by the present method is pancreatic cancer. In other embodiments, the cancer treatable by the present method is liver cancer. In further embodiments, the cancer treatable by the present method is brain tumor.

According to preferred embodiments of the present disclosure, the cancer is resistant to the anti-cancer agent.

According to some embodiments of the present disclosure, the subject has the pancreatic cancer that is resistant to gemcitabine, and the cancer is more susceptible to gemcitabine during, before or after the subject is treated with the sensitizer that comprises MBZ and CQ.

According to optional embodiments of the present disclosure, the subject has the gemcitabine resistant pancreatic cancer, which is more susceptible to gemcitabine during, before or after the subject is treated with the sensitizer that comprises MBZ, CQ and 4-PB.

According to some embodiments of the present disclosure, the subject has the liver cancer, which is more susceptible to doxorubicin during, before or after the subject is treated with the sensitizer that comprises MBZ and CQ.

According to some embodiments of the present disclosure, the subject has the liver cancer, which is more susceptible to sorafenib during, before or after the subject is treated with the sensitizer that comprises MBZ and HCQ.

According to further embodiments of the present disclosure, the subject has the brain tumor, which is more susceptible to TMZ during, before or after the subject is treated with the sensitizer that comprises MBZ and CQ.

The details of one or more embodiments of the invention are set forth in the accompanying description below. Other features and advantages of the invention will be apparent from the detail descriptions, and from claims.

DETAILED DESCRIPTION

Figure 1:
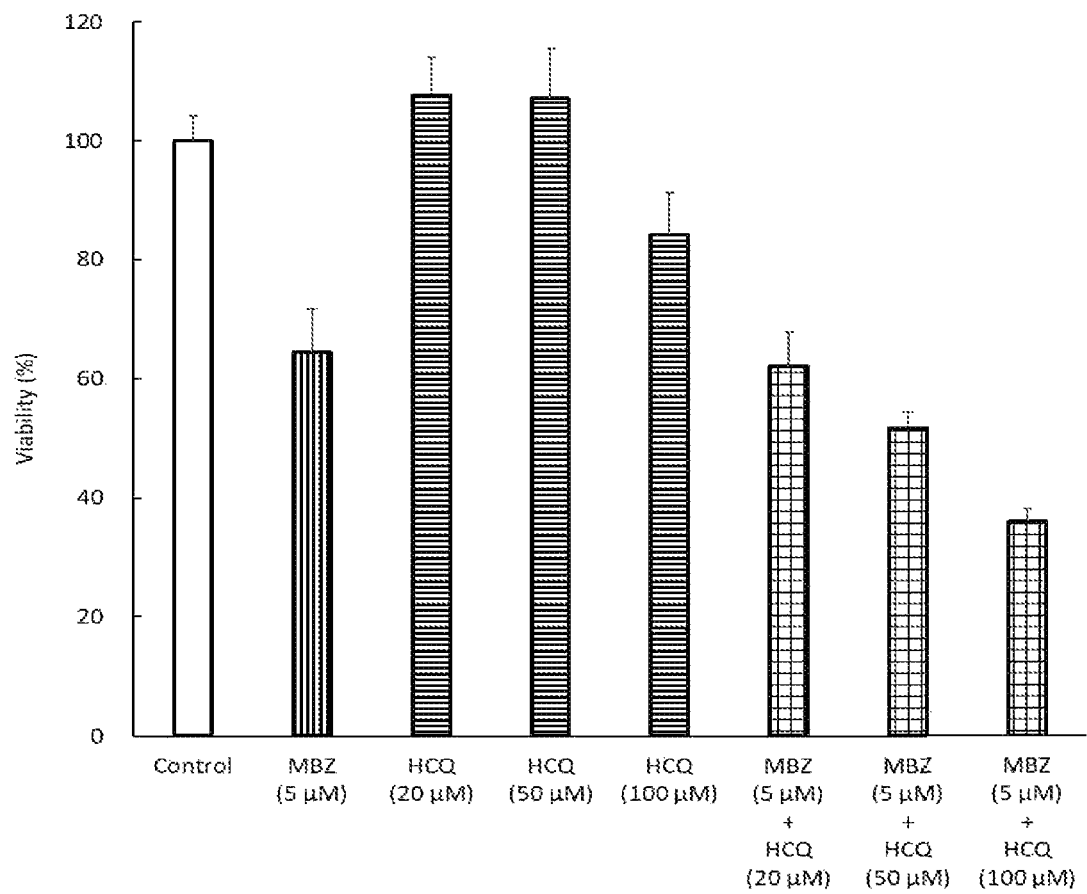
FIG. 1 is a bar graph depicting the effect of MBZ and HCQ on the viability of pancreatic cancer BxPC-3 cells in accordance with one embodiment of the present disclosure.

The detailed description provided below in connection with the appended drawings is intended as a description of the present invention and is not intended to represent the only forms in which the present invention may be constructed or utilized.

1. Definition

For convenience, certain terms employed in the specification, examples and appended claims are collected here. Unless otherwise defined herein, scientific and technical terminologies employed in the present disclosure shall have the meanings that are commonly understood and used by one of ordinary skill in the art.

The term "susceptibility" as used herein regarding a cancer cell, refers to the degree to which a cancer is affected by an anti-cancer agent. The cancer cell may not be affected at all, it may have its growth or proliferation slowed or halted without its being killed, or it may be killed. Susceptibility also refers to the degree a population of cancer cells, such as a tumor, is affected by an anti-cancer agent. "Enhancing susceptibility" of a cancer to an anti-cancer agent following contact or treatment with the present sensitizer, i.e., a combination of an anti-parasitic agent and an autophagy inhibitor, and optionally a histone deacetylase (HDAC) inhibitor, indicates that the cancer cells are more affected by the anticancer agent than corresponding cancer cells that have not been exposed to the agent.

The term "an effective amount" as used herein refers to an amount effective, at dosages, and for periods of time necessary, to achieve the desired result with respect to the reduced viability of a cancer or the enhanced susceptibility of a cancer, particularly, a drug resistant cancer, in a subject to an anti-cancer agent. The specific effective amount will vary with such factors as the particular condition being treated, the physical condition of the patient (e.g., the patient's body mass, age, or gender), the type of mammal or animal being treated, the duration of the treatment, the nature of concurrent therapy (if any), and the specific formulations employed and the structure of the compounds or its derivatives. Effective amount may be expressed, for example, in grams, milligrams or micrograms or as milligrams per body weight (e.g., mg/Kg); or in grams, milligrams or micrograms or as milligrams per day (e.g., mg/day). Alternatively, the effective amount can be expressed in the concentration of the active component (e.g., the present sensitizer or a chemotherapeutic agent), such as molar concentration, mass concentration, volume concentration, molality, mole fraction, mass fraction and mixing ratio. Specifically, the term "effective amount" used in connection with the drug or compounds described herein refers to the quantity of the drug or compounds, which is sufficient to reduce viability of a cancer or increase susceptibility of a cancer to an anti-cancer agent, so as to suppress or inhibit the growth of the cancer. Persons having ordinary skills could calculate the human equivalent dose (HED) for the medicament (such as the sensitizer of the present disclosure) based on the doses determined from animal models set forth in the working examples of the present disclosure. For example, one may follow the guidance for industry published by US Food and Drug Administration (FDA) entitled "Estimating the Maximum Safe Starting Dose in Initial Clinical Trials for Therapeutics in Adult Healthy Volunteers" in estimating a maximum safe dosage for use in human subjects.

When therapies are administered "in combination" (or "combined therapy") means that two (or more) different treatments or agents are delivered to the subject during the course of the subject's affliction with an disorder (e.g., cancer), the two or more treatments or agents are delivered after the subject has been diagnosed with the disorder and before the disorder has been cured or eliminated or treatment has ceased for other reasons. In some embodiments, the delivery of one treatment is still occurring when the delivery of the second begins, so that there is an overlap in terms of administration. This is sometimes referred to herein as "during," "together with" or "concurrently" delivery. In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments or agents can be partially additive, wholly additive, or greater than additive. The delivery can be such that an effect of the first treatment or agent delivered is still detectable when the second is delivered. The determination of the order of treatments is well within the knowledge of the skilled physician after evaluation of the disease being treated and the condition of the subject.

The term "subject" or "patient" refers to an animal including the human species that is treatable with the formulation and/or methods of the present invention. The term "subject" or "patient" intended to refer to both the male and female gender unless one gender is specifically indicated. Accordingly, the term "subject" or "patient" comprises any mammal, preferably a human, which may benefit from the formulations and/or methods of this disclosure.

Also, unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about". Accordingly, unless indicated to the contrary, the numerical parameters set forth in the present disclosure and attaching claims are approximations that can vary as desired. At the very least, each numerical parameter should at least be construed in light of the number of reported significant digits and by applying ordinary rounding techniques.

2. Method of Treating Cancers

The present invention is based, at least in part, on the discovery that certain combination of compounds may reduce viability of cancerous cells, thus are useful for treating cancers. One aspect of the present disclosure lies in providing a method of treating a cancer in a subject. The method includes administering to the subject an effective amount of an anti-parasitic agent and an autophagy inhibitor, so as to reduce the viability of the cancer.

Examples of the anti-parasitic agent suitable for use in the present method include, but are not limited to, albendazole, amphotericin B, benzimidazole, diethylcarbamazine, eflornithine, febantel, fenbendazole, flubendazole, fumagillin, lvermectin, mebendazole (MBZ), melarsopol, metronidazole, miltefosine, netobimin, niclosamide, nitazoxanide, oxfendazole, oxifendazole, oxibendazole, praziquantel, pyrantel pamoate, rifampin, thiabendazole, thiophanate, tinidazole, and triclabendazole.

Examples of the autophagy inhibitor suitable for use in the present method include, but are not limited to, bafilomycin A1, bortezomib, chloroquine (CQ), hydroxychloroquine (HCQ), 3-methyladenine (3-MA) and quinacrine.

According to embodiments of the present disclosure, the cancer treatable by the present method may be bladder cancer, breast cancer, brain tumor, colon cancer, head and neck cancer, leukemia, lung cancer, liver cancer, lymphoma, kidney cancer, melanoma, neuroepithelioma, ovarian cancer, pancreatic cancer, prostate cancer, rectal cancer, stomach cancer, or uterus cancer. In some embodiments, the cancer treatable by the present method is pancreatic cancer. In other embodiments, the cancer treatable by the present method is liver cancer. In further embodiments, the cancer treatable by the present method is brain tumor.

According to embodiments of the present disclosure, the cancer treatable by the present method may be resistant to an anti-cancer agent. Non-limiting examples of anticancer agent include gemcitabine, doxorubicin, sorafenib, and temozolomide (TMZ). In some embodiments, the cancer is resistant to gemcitabine. In other embodiments, the cancer is resistant to sorafenib.

According to some embodiments of the present disclosure, the subject has pancreatic cancer, and the viability of the pancreatic cancer is reduced by the combined treatment of MBZ and CQ, or the combined treatment of MBZ and HCQ.

According to other embodiments of the present disclosure, the subject has gemcitabine resistant pancreatic cancer, and the viability of the gemcitabine resistant pancreatic cancer is reduced by the combined treatment of MBZ and CQ, or the combined treatment of MBZ and HCQ.

According to further embodiments of the present disclosure, the subject has liver cancer, and the viability of the liver cancer is reduced by the combined treatment of MBZ and CQ, or the combined treatment of MBZ and HCQ.

According to further embodiments of the present disclosure, the subject has brain cancer, and the viability of the brain cancer is reduced by the combined treatment of MBZ and CQ, or the combined treatment of MBZ and HCQ.

3. Method of Enhancing Susceptibility of a Cancer to Anti-Cancer Agent

The present invention is based, at least in part, on the discovery that certain combination of compounds may enhance susceptibility of a cancer, particularly, a drug-resistant cancer, to an anti-cancer agent (e.g., chemotherapy). Thus, the present invention not only allows drug-resistant cancer to be treated, but also allows lower doses of anti-cancer agent to be used on cancer that can be treated by the anti-cancer agent.

Accordingly, the second aspect of the present disclosure lies in providing a method of enhancing susceptibility of a cancer in a subject to an anti-cancer agent.

In the treatment of a cancer fails to respond (or resistant) to an anti-cancer agent (e.g., chemotherapeutic agent), a sensitizer is administered before, together with, or after the anti-cancer agent is administered to the subject.

According to embodiments of the present disclosure, the sensitizer is comprised of at least two agents selected from the group consisting of an anti-parasitic agent, an autophagy inhibitor, and a histone deacetylase (HDAC) inhibitor.

Exemplary anti-parasitic agent suitable for use in the present invention includes, but is not limited to, albendazole, amphotericin B, benzimidazole, diethylcarbamazine, eflornithine, febantel, fenbendazole, flubendazole, fumagillin, Ivermectin, mebendazole (MBZ), melarsopol, metronidazole, miltefosine, netobimin, niclosamide, nitazoxanide, oxfendazole, oxifendazole, oxibendazole, praziquantel, pyrantel pamoate, rifampin, thiabendazole, thiophanate, tinidazole, and triclabendazole.

Exemplary autophagy inhibitor suitable for use in the present invention includes, but is not limited to, bafilomycin A1, bortezomib, CQ, HCQ, 3-MA and quinacrine.

Exemplary HDAC inhibitor suitable for use in the present invention includes, but is not limited to, belinostat, 4-phenylbutyrate (4-PB), romidepsin, and vorinostat.

In some embodiments, the sensitizer is comprised of the anti-parasitic agent (e.g., MBZ) and the autophagy inhibitor.

In other embodiments, the sensitizer is comprised of the anti-parasitic agent (e.g., MBZ), the autophagy inhibitor (e.g., CQ) and the HDAC inhibitor (e.g., 4-PB).

According to embodiments of the present disclosure, the cancer is unresponsive or resistant to an anti-cancer agent (e.g., chemotherapeutic agent), which may be any of gemcitabine, doxorubicin, sorafenib, and temozolomide (TMZ). According to preferred embodiments of the present disclosure, the cancer is unresponsive or resistant to gemcitabine.

Exemplary cancer that may be treated by the present method includes, but is not limited to, bladder cancer, breast cancer, brain tumor, colon cancer, head and neck cancer, leukemia, lung cancer, liver cancer, lymphoma, kidney cancer, melanoma, neuroepithelioma, ovarian cancer, pancreatic cancer, prostate cancer, rectal cancer, stomach cancer, and uterus cancer. In some embodiments, the cancer is pancreatic cancer. In further embodiments, the pancreatic cancer is resistant to gemcitabine.

In certain embodiments, the subject has pancreatic cancer and is unresponsive or resistant to the treatment of gemcitabine, thus, the sensitizer comprising MBZ and CQ is administered together with gemcitabine to the subject to enhance the susceptibility of the cancer to gemcitabine. Optionally or alternatively, the sensitizer comprising MBZ, CQ and 4-PB is administered together with gemcitabine to the subject to enhance the susceptibility of the cancer to gemcitabine.

A skilled person will be aware that the sensitizer described herein may be administered in any suitable manner. For example, the administration may be parenteral, such as intravenous or subcutaneous, oral, transdermal, intranasal, by inhalation, or rectal. In some preferred embodiments, the sensitizer is administered orally. In other preferred embodiments, the sensitizer is administered by injection.

The dose of the sensitizer administered to the subject, particularly a human, in the context of the present invention should be sufficient to effect a therapeutic response (e.g., suppression or inhibition of the growth of the cancer, and/or reduction the size of the cancer) in the subject over a reasonable time frame. One skilled in the art will recognize that suitable dosage depends upon a variety of factors including the age, sex, condition and body weight of the patient, as well as the stage/severity of the disease. The dose will also be determined by the route, timing and frequency of administration. In the case of oral administration, the dosage for the sensitizer can vary from about 0.01 mg to about 10 g, preferably from about 1 mg to about 8 g, preferably from about 10 mg to about 5 g, more preferably from about 10 mg to about 2 g, more preferably from about 100 mg to about 1 g per day of the compound (e.g., the anti-parasitic agent, the HDAC inhibitor, the autophagy inhibitor, and/or a combination thereof). The attending clinician, in judging whether treatment is effective at the dosage administered, will consider the general well-being of the subject as well as more definite signs such as relief of disease-related symptoms, inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

Alternatively or optionally, the method described herein may be used in further combination with other known therapies, including surgery, radiation, cryosurgery, and/or thermotherapy. The effect of the two treatments can be partially additive, wholly additive, or greater than additive. Such combination therapies may advantageously use lower dosages of the administered agent and/or other chemotherapeutic agent, thus avoiding possible toxicities or complications associated with the combination therapies. The term "radiation" includes, but is not limited to, external-beam therapy which involves three dimensional, conformal radiation therapy where the field of radiation is designed to conform to the volume of tissue treated; interstitial-radiation therapy where seeds of radioactive compounds are implanted using ultrasound guidance; and a combination of external-beam therapy and interstitial-radiation therapy. The particular choice of additional treatment will depend upon the diagnosis of the attending physicians and their judgment of the condition of the subject and the appropriate treatment protocol. The determination of the order of administration, and the number of repetitions of administration of each therapeutic agent during a treatment protocol, is web within the knowledge of the skilled physician after evaluation of the disease being treated and the condition of the subject.

4. Formulations for Reducing Viability of a Cancer and/or Enhancing Susceptibility of a Cancer to Anti-Cancer Agent A further aspect of the present disclosure is to provide formulations for use in the present method. In some embodiments, the afore-described sensitizer (e.g., at least two agents that is any of an anti-parasitic agent, an autophagy inhibitor, and an HDAC inhibitor) suitable for enhancing susceptibility of a cancer to an anti-cancer agent are formulated into dosage forms for administering to the subject.

The present formulation comprises an effective amount of at least two agents selected from the group consisting of an anti-parasitic agent, an autophagy inhibitor, and an HDAC inhibitor; and a pharmaceutically acceptable excipient. For example, the anti-parasitic agent (e.g., MBZ) and the autophagy inhibitor (e.g., CQ/HCQ) may be mixed with pharmaceutically acceptable excipients to form a formulation for administering to the subject.

In some embodiments, the formulation comprises the anti-parasitic agent (e.g., MBZ), the autophagy inhibitor (e.g., CQ), and the HDAC inhibitor (e.g., 4-PB); and a pharmaceutically acceptable excipient. In still further embodiments, the formulation comprises the HDAC inhibitor (e.g., 4-PB), the anti-parasitic agent (e.g., MBZ), and the autophagy inhibitor (e.g., HCQ); and a pharmaceutically acceptable excipient.

The sensitizers are present at a level of about 0.1% to 99% by weight, based on the total weight of the formulation. In some embodiments, the sensitizers are present at a level of at least 1% by weight, based on the total weight of the formulation. In certain embodiments, the agents are present at a level of at least 5% by weight, based on the total weight of the formulation. In still other embodiments, the agents are present at a level of at least 10% by weight, based on the total weight of the formulation. In still yet other embodiments, the agents are present at a level of at least 25% by weight, based on the total weight of the formulation.

The formulation is prepared in accordance with acceptable pharmaceutical procedures, such as described in Remington's Pharmaceutical Sciences, 17$^{th}$ edition, ed. Alfonoso R. Gennaro, Mack Publishing Company, Easton, Pa (1985). Pharmaceutically acceptable excipients are those that are compatible with other ingredients in the formulation and biologically acceptable.

The formulation is manufactured in accordance with the intended routes for its administration. For example, if the formulation is intended to be administered by oral ingestion, an enteric coating may be applied on the formulation so as to prevent the compound of the present invention from being degraded in the acidic environment or until it reaches the intestines of the subject. The formulation may further include additional components that help deliver the compound of the present invention to its intended target site. In some examples, the agents constituted the sensitizer is enclosed in a liposome to prevent it from enzymatic degradation, and to help transporting the agents through the circulation system of the subject, and/or across cell membrane to its intended cellular target site.

Further, the least soluble agent of the sensitizer may be formulated with additional agents, such as a solvating agent, an emulsifying agent and/or a surfactant, into a liquid formulation. Examples of the additional agent include, but are not limited to, cyclodextrin (e.g., α-cyclodextrin and β-cyclodextrin), and non-aqueous solvents, which include but are not limited to, ethanol, isopropanol, ethyl carbonate, ethyl acetate, benzyl alcohol, benzyl benzoate, propyl glycol, 1,3-butyl glycol, dimethyl formamide, dimethyl sulfoxide, biocompatible oils (e.g., cottonseed oil, peanut oil, corn oil, wheat germ oil, castor oil, olive oil, sesame oil, glycerol, tetrahydrogen furan, polyethylene glycol (PEG), fatty acid esters of sorbitan, and a combination thereof).

The amount of the sensitizer in the formulation varies with the route of administration. For example, formulations for acute treatment will contain larger amounts of the sensitizer, as compared to formulations that are for chronic treatment. Similarly, parental formulations will comprise less amounts of the present sensitizer, as compared to formulations that are for oral ingestion. Also within the scope of the present disclosure are formulations suitable for other administration routes.

Formulations may be in the form of liquids, solutions, suspensions, emulsions, elixirs, syrups, tablets, lozenges, granules, powders, capsules, cachets, pills, ampoules, suppositories, pessaries, ointments, gels, pastes, creams, sprays, mists, foams, lotions, oils, boluses, electuaries, or aerosols.

4.1 Formulation for Oral Ingestion

The present sensitizer (i.e., at least two agents selected from the group consisting of an anti-parasitic agent, an autophagy inhibitor, and an HDAC inhibitor) may be formulation into compositions suitable for oral ingestion. Formulations suitable for oral administration (e.g. by ingestion) may be presented as discrete units such as capsules, cachets or tablets, each containing a predetermined amount of the active compound; as a powder or granules; as a solution or suspension in an aqueous or non-aqueous liquid; or as an oil-in-water liquid emulsion or a water-in-oil liquid emulsion; as a bolus; as an electuary; or as a paste.

A tablet may be made by conventional means, e.g., compression or molding, optionally with one or more accessory ingredients. Compressed tablets may be prepared by compressing in a suitable machine the active compound in a free-flowing form such as a powder or granules, optionally mixed with one or more binders (e.g. povidone, gelatin, acacia, sorbitol, tragacanth, hydroxypropylmethyl cellulose); fillers or diluents (e.g. lactose, microcrystalline cellulose, calcium hydrogen phosphate); lubricants (e.g. magnesium stearate, talc, silica); disintegrants (e.g. sodium starch glycolate, cross-linked povidone, cross-linked sodium carboxymethyl cellulose); surface-active or dispersing or wetting agents (e.g. sodium lauryl sulfate); and preservatives (e.g. methyl p-hydroxybenzoate, propyl p-hydroxybenzoate, sorbic acid). Molded tablets may be made by molding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with an enteric coating, to provide release in parts of the gut other than the stomach.

4.2 Formulation for Parental Administration

Formulations suitable for parenteral administration (e.g., by injection, including cutaneous, subcutaneous, intramuscular, intravenous and intradermal), include aqueous and nonaqueous isotonic, pyrogen-free, sterile injection solutions which may contain antioxidants, buffers, preservatives, stabilizers, bacteriostats, and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such formulations include Sodium Chloride Injection, Ringer's Solution, or Lactated Ringer's Injection. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other nanoparticulate or microparticulate systems which are designed to target the active compound to blood components or one or more organs.

4.3 Transmembrane Formulation

Transmembrane formulations are those suitable for topical and tansmucosal uses, which include but are not limited to, ophthalmic solutions, sprays, aerosols, creams, lotions, ointments, gels, solutions, suspensions, skin patches and the like. The patches include reservoir type and matrix type skin patches, and may adhere onto the skin for a certain period of time to allow the active component to be adsorbed into the subject's body.

For topical administration, a wide variety of dermatologically acceptable inert excipients well known to the art may be employed. Typical inert excipients may be, for example, water, ethyl alcohol, polyvinyl pyrrolidone, propylene glycol, mineral oil, stearyl alcohol and gel-producing substances. All of the above dosages forms and excipients are well known to the pharmaceutical art. The choice of the dosage form is not critical to the efficacy of the composition described herein.

For transmucosal administration, the present sensitizer (e.g., the HDAC inhibitor and at least one agent selected from the group consisting of the anti-parasitic agent and the autophagy inhibitor) may also be formulated in a variety of dosage forms for mucosal application, such as buccal and/or sublingual drug dosage units for drug delivery through oral mucosal membranes. A wide variety of biodegradable polymeric excipients may be used that are pharmaceutically acceptable, provide both a suitable degree of adhesion and the desired drug release profile, and are compatible with the active agents to be administered and any other components that may be present in the buccal and/or sublingual drug dosage units. Generally, the polymeric excipient comprises hydrophilic polymers that adhere to the wet surface of the oral mucosa. Examples of polymeric excipients include, but are not limited to, acrylic acid polymers and copolymers; hydrolyzed polyvinyl alcohol; polyethylene oxides; polyacrylates; vinyl polymers and copolymers; polyvinylpyrrolidone; dextran; guar gum; pectins; starches; and cellulosic polymers.

5. Kits for Reducing Viability of a Cancer and/or Enhancing Susceptibility of a Cancer to an Anti-Cancer Agent Also encompasses within the present disclosure is an article of manufacture or "kit," containing materials useful for the treatment of a cancer, particularly, a cancer that is unresponsive to chemotherapy.

In one embodiment, the kit comprises a container comprising the sensitizer of the present disclosure formulated into suitable form for administering to a subject in need thereof. The kit is suitable for reducing viability of a cancer or enhancing susceptibility of a cancer to an anti-cancer agent, thus is administered before, during or after the administration of the anti-cancer agent. The container may be formed from a variety of materials such as glass, or plastic. The container may hold a pharmaceutical formulation of the present sensitizer in an amount effective for the treatment of a cancer unresponsive to chemotherapy. Optionally, the container may have a sterile access port, for example, the container may be an intravenous solution bag or a vail having a stopper pierceable by a hypodermic injection needle. The kit may further comprise a label or package insert on or associated with the container. The label or package insert indicates that the composition is used for treating a condition of choice. Alternatively or additionally, the kit may further comprise a second container comprising a pharmaceutically acceptable buffer, such as a phosphate-buffered saline, Ringer's solution or dextrose solution. It may further include other materials desirable from a commercial and user standpoint, including other buffers, diluents, filters, needles, and syringes.

The kit may further include directions for the administration of the sensitizer of the present invention and, if present, the second formulation for treating the cancer. For example, if the kit comprises a first composition comprising the sensitizer of the present disclosure, and a second pharmaceutical formulation comprising a therapeutic agent, the kit may further include directions for the simultaneous, sequential, or separate administration of the first and second pharmaceutical compositions to a patient in need thereof.

In another embodiment, the kits are suitable for the delivery of solid oral forms of the present sensitizer, such a kit includes, for example, a number of unit dosages. Such kits include card having the dosages oriented in the order of their intended use. An example of such kit is a "blister pack." Blister packs are well known in the packaging industry and are widely used for packaging pharmaceutical unit dosage forms. If desired, an aid may be provided, for example, in the form of numbers, letters, or other markings or with a calendar insert, designating the days in the treatment schedule in which the dosage can be administered.

According to one embodiment, the Kit may include, at least, (a) a first container containing the present sensitizer formulated into suitable form for administering to a subject; and optionally, (b) a second container containing a second formulation that is a chemotherapeutic agent; and (c) a legend associated with the kit for instructing a user how to use the kit. The legend may be in a form of pamphlet, tape, CD, VCD or DVD.

The present invention will now be described more specifically with reference to the following embodiments, which are provided for the purpose of demonstration rather than limitation.

EXAMPLES

Materials and Methods

Cell Culture and Animals

Cell lines used in the present disclosure include human pancreatic cancer cell lines BxPC-3, Mia-Paca-2/R (gemcitabine resistant cell line), and Panc-1/R (gemcitabine resistant cell line); human liver cancer cell lines SK-Hep-1 and Hep 3B; and human brain glioblastoma cell line GBM8401, which is a TMZ-resistant cell line. Cells were cultured in Dulbecco's modified Eagle media (DMEM) supplemented with 10% heat inactivated fetal bovine serum (FBS), 50 units/mL penicillin G, 50 m/mL streptomycin (pH 7.4), and the cells were maintained in humidified environment comprising 5% $CO_2$/95% air at 37° C.

Induction of Drug Resistant Panc-1 Cells

The drug resistant Panc-1/Gem cells were induced by culturing Panc-1 cells in the presence of a continuous low dose of gemcitabine (20 μM) to generate their resistance to gemcitabine. In operation, gemcitabine resistant Panc-1 cells (Panc-1/Gem) were maintained in the DMEM supplemented with 10% fetal calf serum (FCS), 100 IU/ml penicillin, 100 m/ml streptomycin, 2 mM glutamine and 20 μM gemcitabine in 5% $CO_2$ at 37° C.

MTT Assay

MTT assay is a colorimetric assay that measures the activity of enzymes (i.e., reductase) that reduce (3-(4,5-dimethylthiazol-2yl)-2,5-diphenyltetrazoliumbromide (MTT), a yellow tetrazole, to purple formazan, in living cells. This reduction only takes place when cells are alive; hence MTT assay is generally used to assess the viability and proliferation of cells. Briefly, cells were challenged with various doses of the tested compound (e.g., MB, 4-PB, CQ, HCQ, and etc) for 48 or 72 hours. Then, MTT dye (500 m/ml) was added and the reaction was allowed to proceed for 4 hours before being terminated by the addition of 500 μl of isopropanol. The absorbance of the solution at 570 nm was measured by spectrophotometer.

Xenograft Pancreatic Cancer Mice Model

For primary pancreatic cancer model, total of 30 mice at the age of xx weeks were randomly divided into 6 groups, with 5 mice in each group. To start the experiment, each mice were injected with $7 \times 10^6$ Mia-Paca-2/R cells subcutaneously to generate drug resistant pancreatic cancer on day 0, and then returned to culture for another 14 days to allow tumor progression to about 200 mm³ in size. To evaluate the efficacy of the test compounds, mice in the test group were given gemcitabine (50 mg/Kg/dose, i.p., once per week), MBZ (100 mg/Kg/dose, oral, three times per week); CQ (100 mg/Kg/dose, oral, three times per week); MBZ+CQ (oral, three times per week); or MBZ+CQ+gemcitabine (MBZ and CQ were orally administered at the frequency of 3 times/week, gemcitabine was administered once per week via injection) during a period of 28 days after treatment started on day 2. Tumor sizes were measured using calipers. The body weight and the white blood cell counts of each mice were respectively recorded every day throughout the experiment. Tumor volume was calculated using the formula: volume=width²×length×0.52.

EXAMPLES

Example 1 Combined Treatment of Anti-Parasitic Agent and Autophagy Inhibitor Suppresses the Growth of Cancerous Cells Effects of the combined treatment of MBZ and HCQ/CQ on the cell viability of pancreatic cancer BxPC-3 cells, drug resistant pancreatic cancer Mia-Paca-2/R cells, and glioblastoma GBM8401 cells were investigated by MTT assay. Results are illustrated in FIGS. 1 to 3.

1.1 Combined Treatment of MBZ and CQ/HCQ on Cancer Cells

Reference is first made to FIG. 1, which depicts the cell viability of pancreatic cancer BxPC-3 cells after the combined treatment of MBZ (5 μM) and HCQ (50 or 100 μM). It was found that cell viability of BxPC-3 cells was slightly and/or unaffected by the treatment of HCQ (20 or 50 μM) alone. When BxPC-3cells were treated with a combination of MBZ (5 μM), cell viability dropped to about 60%. Surprisingly, when BxPC-3 cells were simultaneously treated with MBZ (5 μM) and HCQ (50 or 100 μM), cell viability was further reduced to a low level of about 55-38%, as compared to that of the control.

Figure 2A:
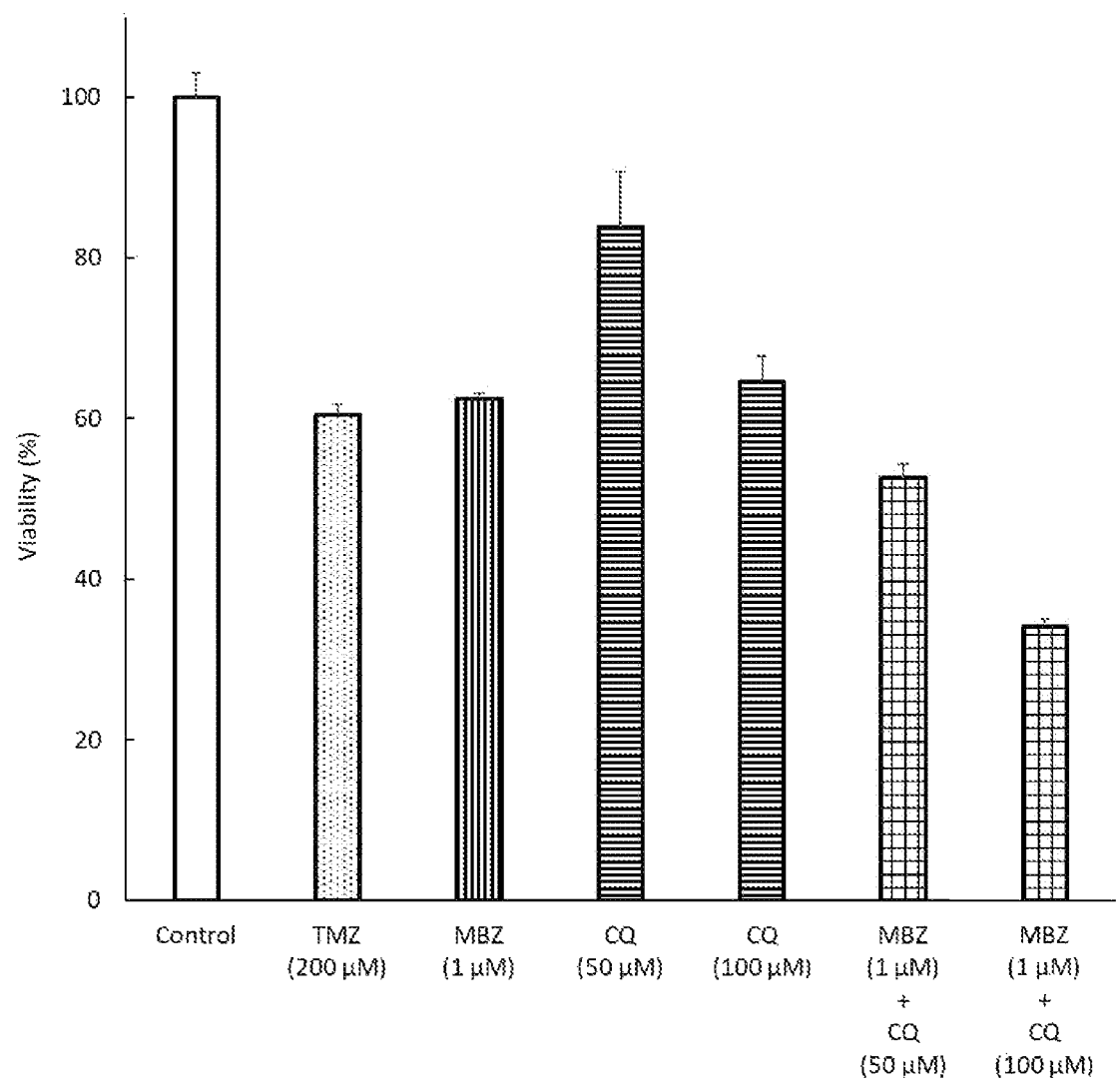
FIGS. 2A and 2B are bar graphs depicting the effect of MBZ and CQ on the viability of glioblastoma GBM8401 cells in accordance with one embodiment of the present disclosure.
Figure 2B:
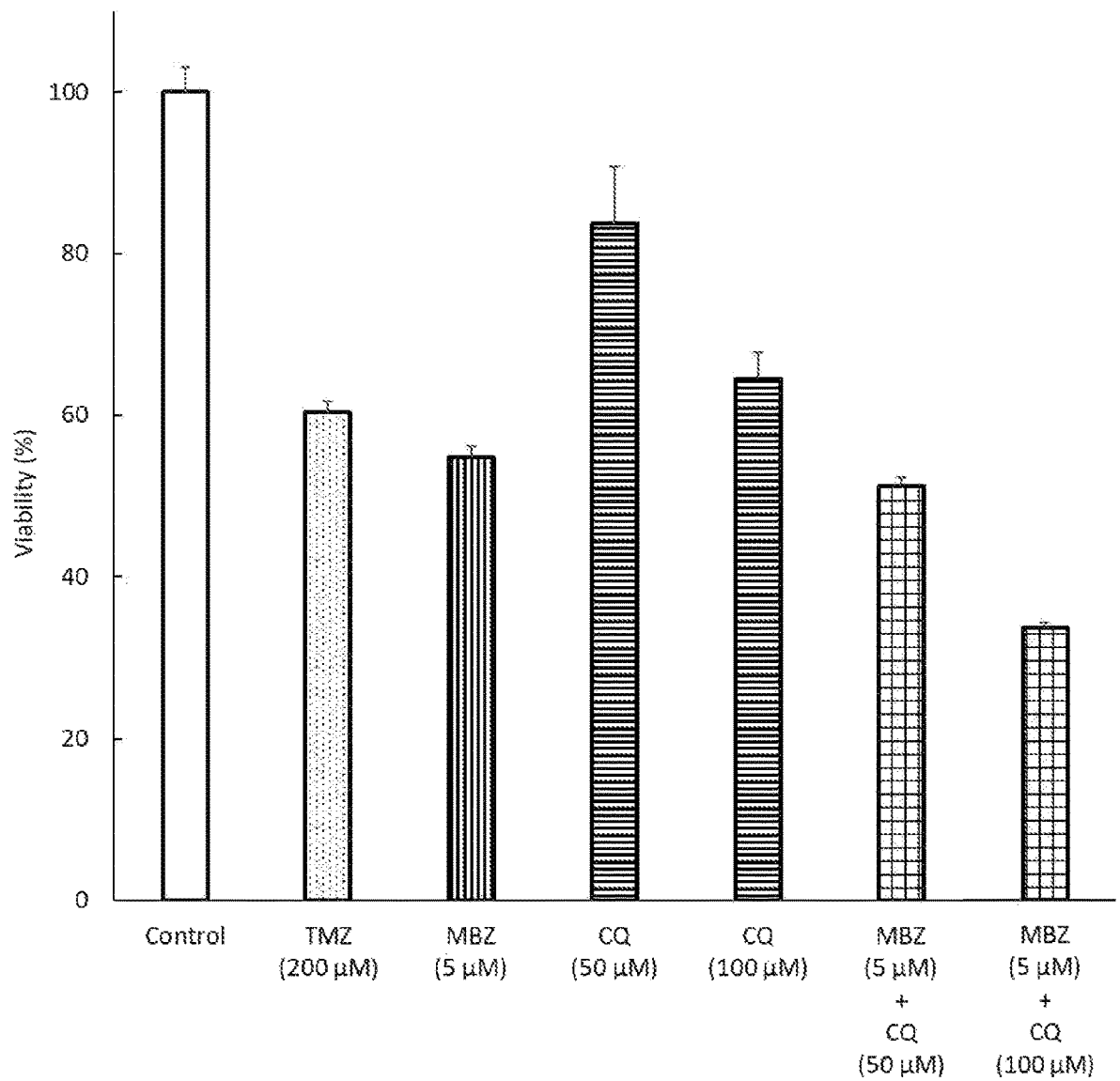
Figure 3:
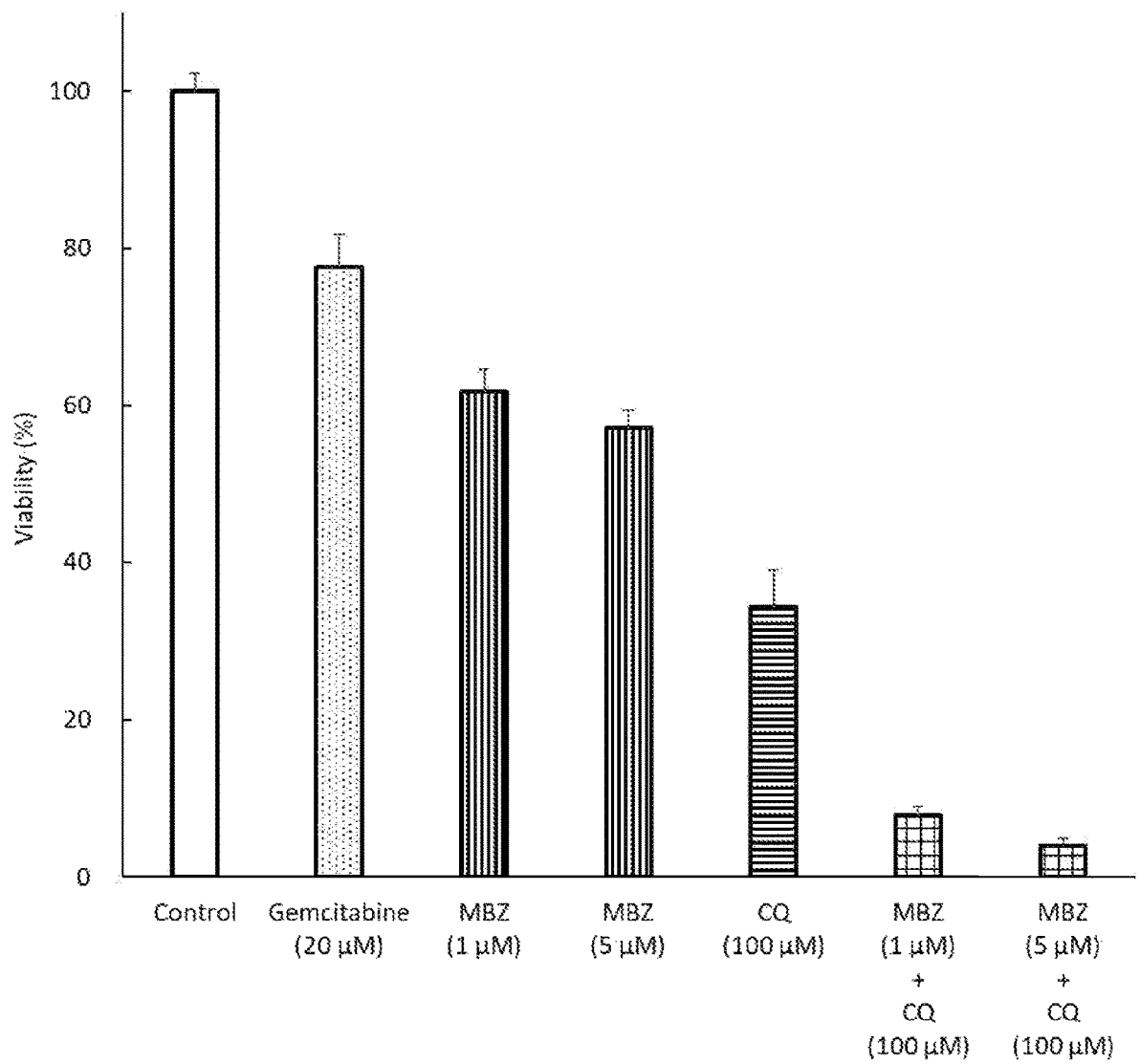
FIG. 3 is a bar graph depicting the effect of MBZ and CQ on the viability of pancreatic drug resistant cancer Mia-Paca-2/R cells in accordance with another embodiment of the present disclosure.

Similar results were also found in glioblastoma GBM8401 cells, in which cell viability of GBM8401 cells was further reduced after the combined treatment of MBZ (5 μM) and CQ (50 or 100 μM) (FIGS. 2A and 2B).

1.2 Combined Treatment of MBZ and HCQ on Drug Resistant Cancer Cells

Effects of the combined treatment of MBZ and CQ on the cell viability of drug resistant pancreatic cancer Mia-Paca-2/R cells was investigated, and results is illustrated in FIG. 3.

As depicted in FIG. 3, the cell viability of drug resistant pancreatic cancer Mia-Paca-2/R cells reached a significant low level of about 10% after the combined treatment of MBZ (1 or 5 μM) and CQ (100 μM), as compared to that of the contriol, or treatment with gencitabine (20 μM), MBZ, or CQ alone.

Example 2 the Present Sensitizer Increases the Susceptibility of Cancer Cells Toward Anti-Cancer Agents Effects of the present sensitizer on the cell viability of pancreatic cancer BxPC-3 cells, drug resistant pancreatic cancer Mia-Paca-2/R cells, Pan-1/Gem cells, hepatoma Sk-Hep-1 cells, or glioblastoma GBM8401 cells toward anti-cancer agent (e.g., gemcitabine, doxorubicin, sorafenib, or TMZ) were investigated by MTT assay. Results are illustrated in FIGS. 4 to 9.

2.1 Combined Use of MBZ and CQ on Cancer Cells

Figure 4:
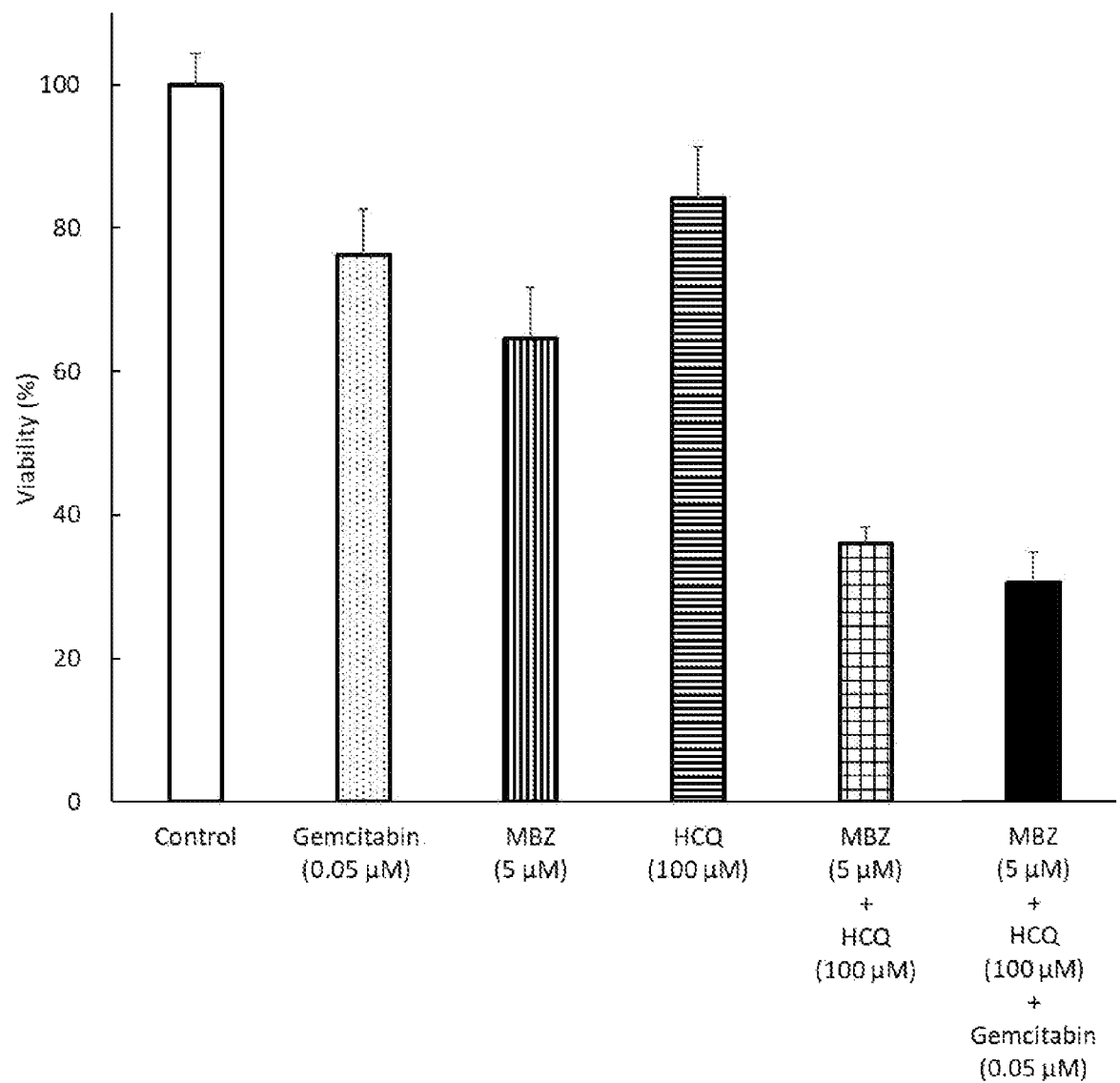
FIG. 4 is a bar graph depicting the cell viability of BxPC-3 cells towards gemcitabine (0.05 µM), after the treatment of the present sensitizer, which comprised MBZ (5 µM) and CQ (100 µM), in accordance with one embodiment of the present disclsoure.
Figure 5:
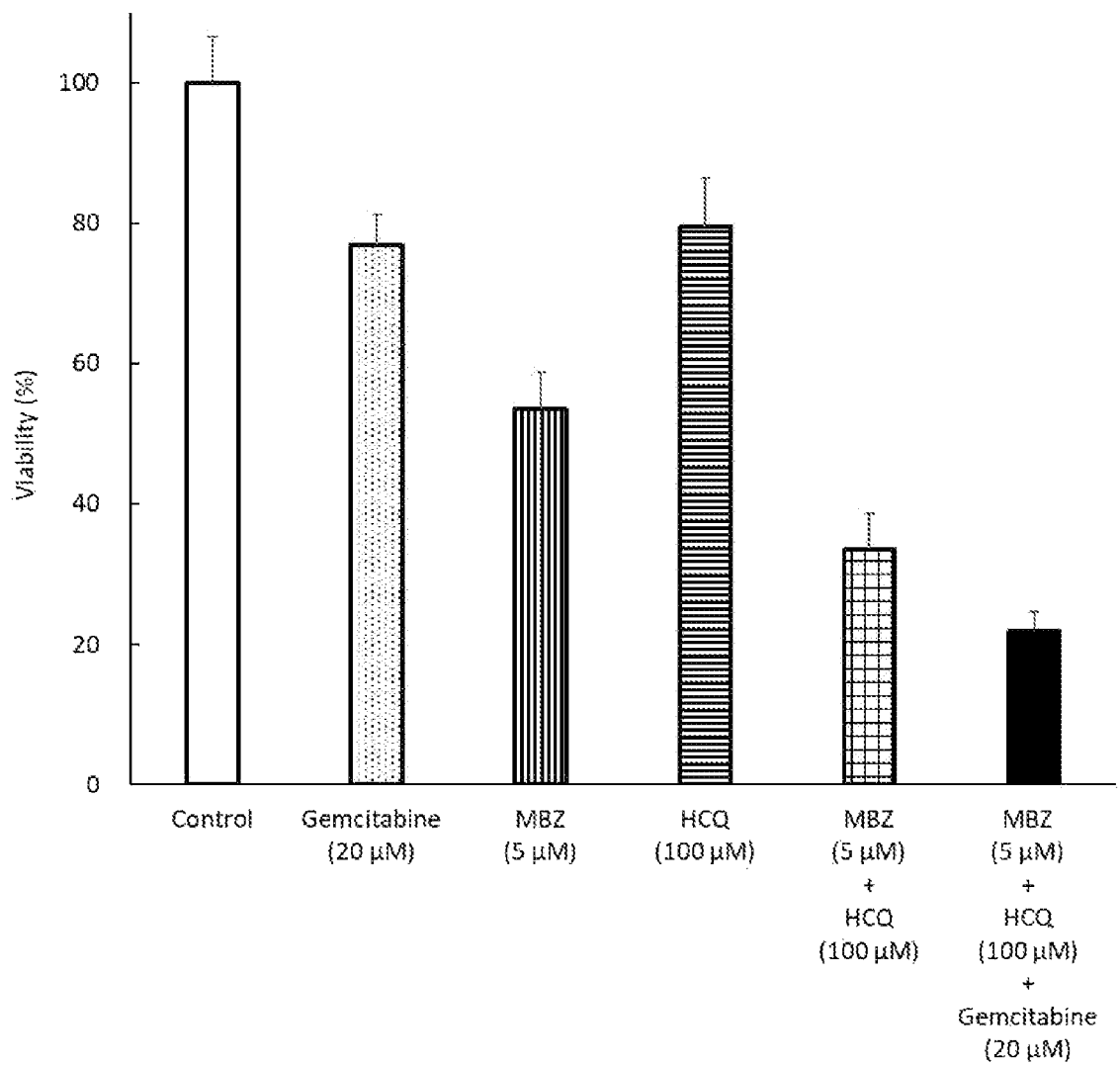
FIG. 5 is a bar graph depicting the cell viability of drug resistant Mia-Paca-2/R cells towards gemcitabine (20 µM), after the treatment of the present sensitizer, which comprised MBZ (5 µM) and HCQ (100 µM), in accordance with one embodiment of the present disclsoure.
Figure 6:
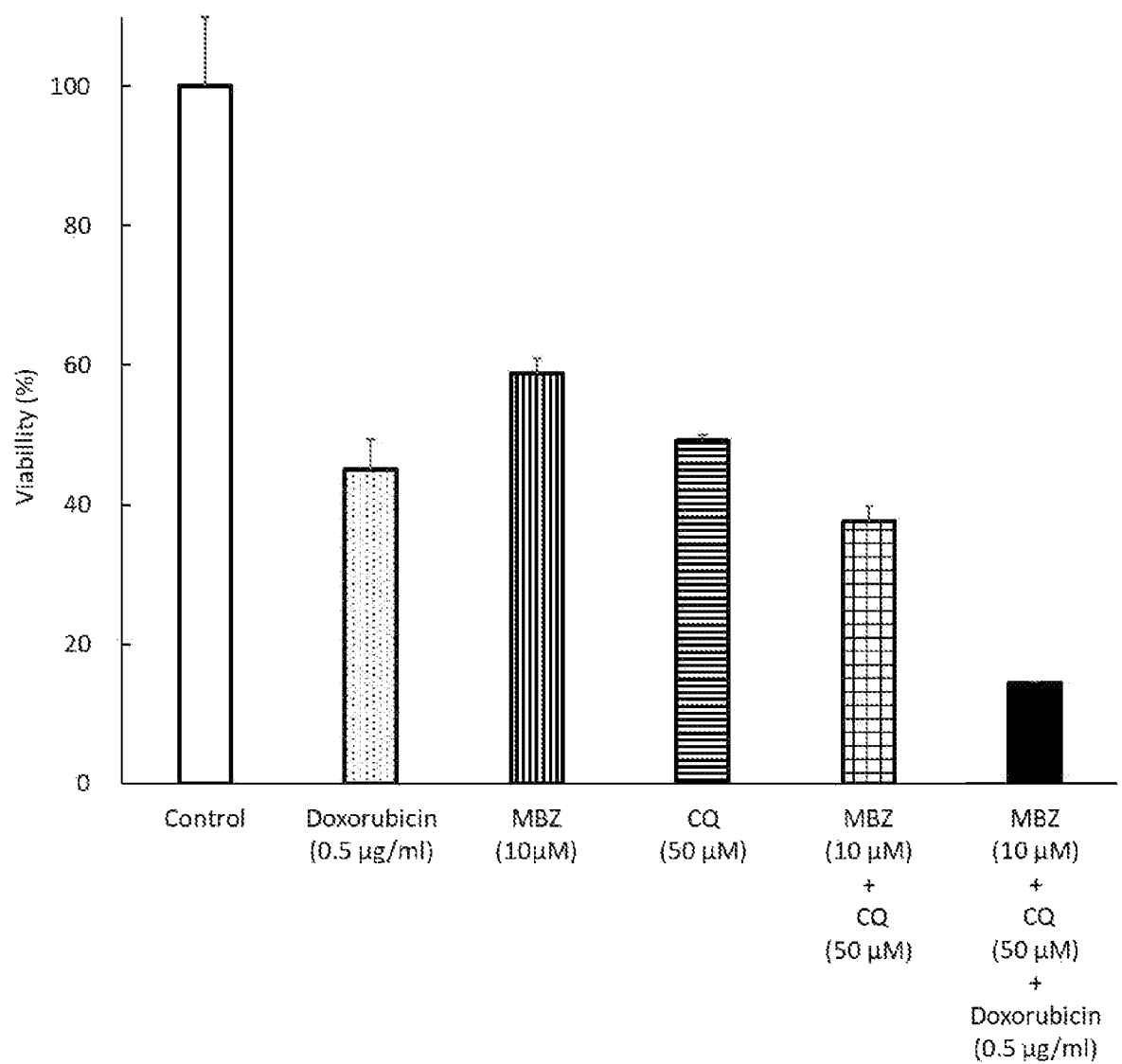
FIG. 6 is a bar graph depicting the cell viability of hepatoma SK-Hep-1 cells towards doxorubicin (0.5 µg/mL), after the treatment of the present sensitizer, which comprised MBZ (10 µM) and CQ (50 µM), in accordance with one embodiment of the present disclsoure.
Figure 7:
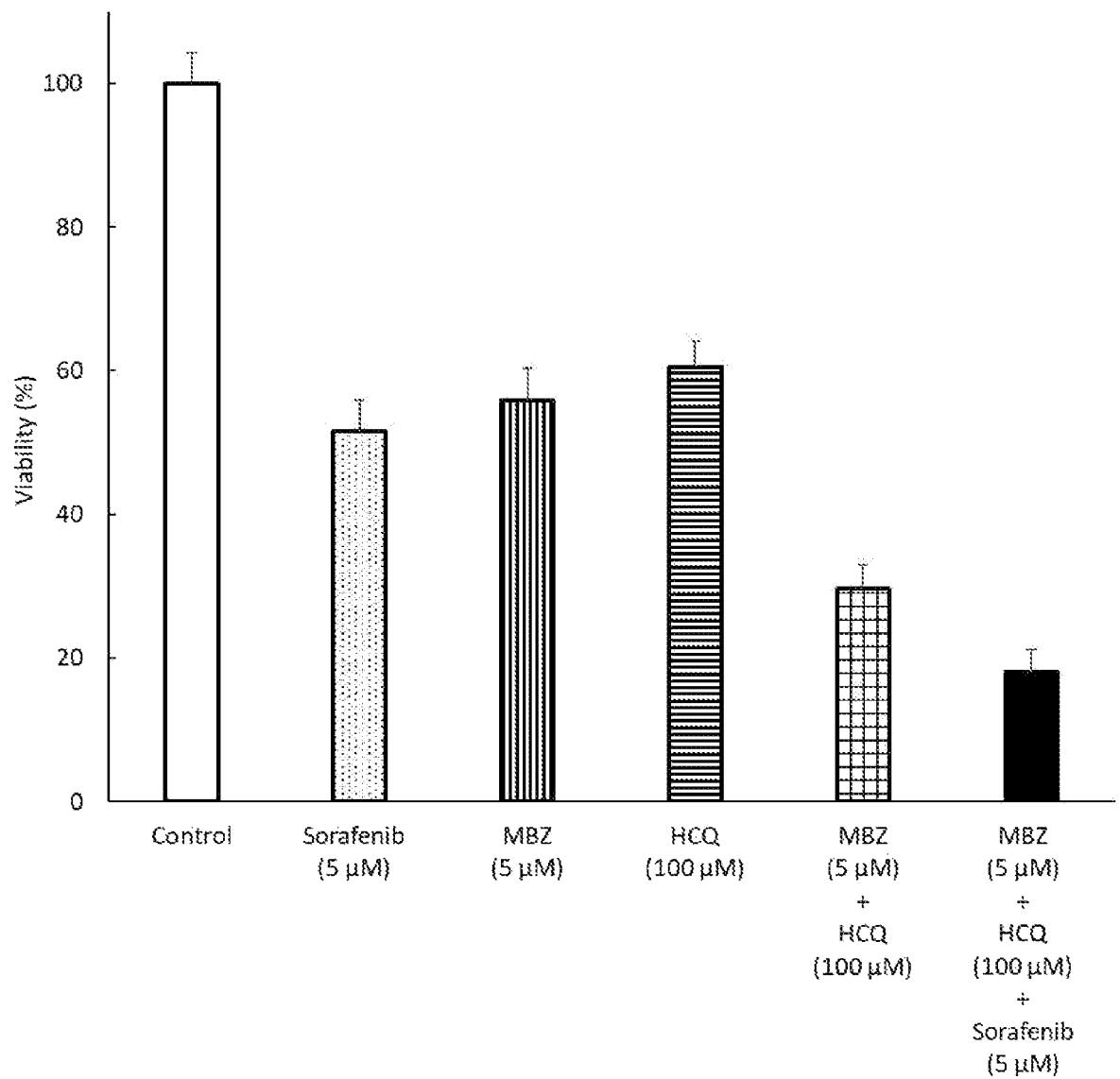
FIG. 7 is a bar graph depicting the cell viability of hepatoma Hep-3B cells towards sorafenib (5 µM), after the treatment of the present sensitizer, which comprised MBZ (5 µM) and HCQ (100 µM), in accordance with one embodiment of the present disclsoure.
Figure 8A:
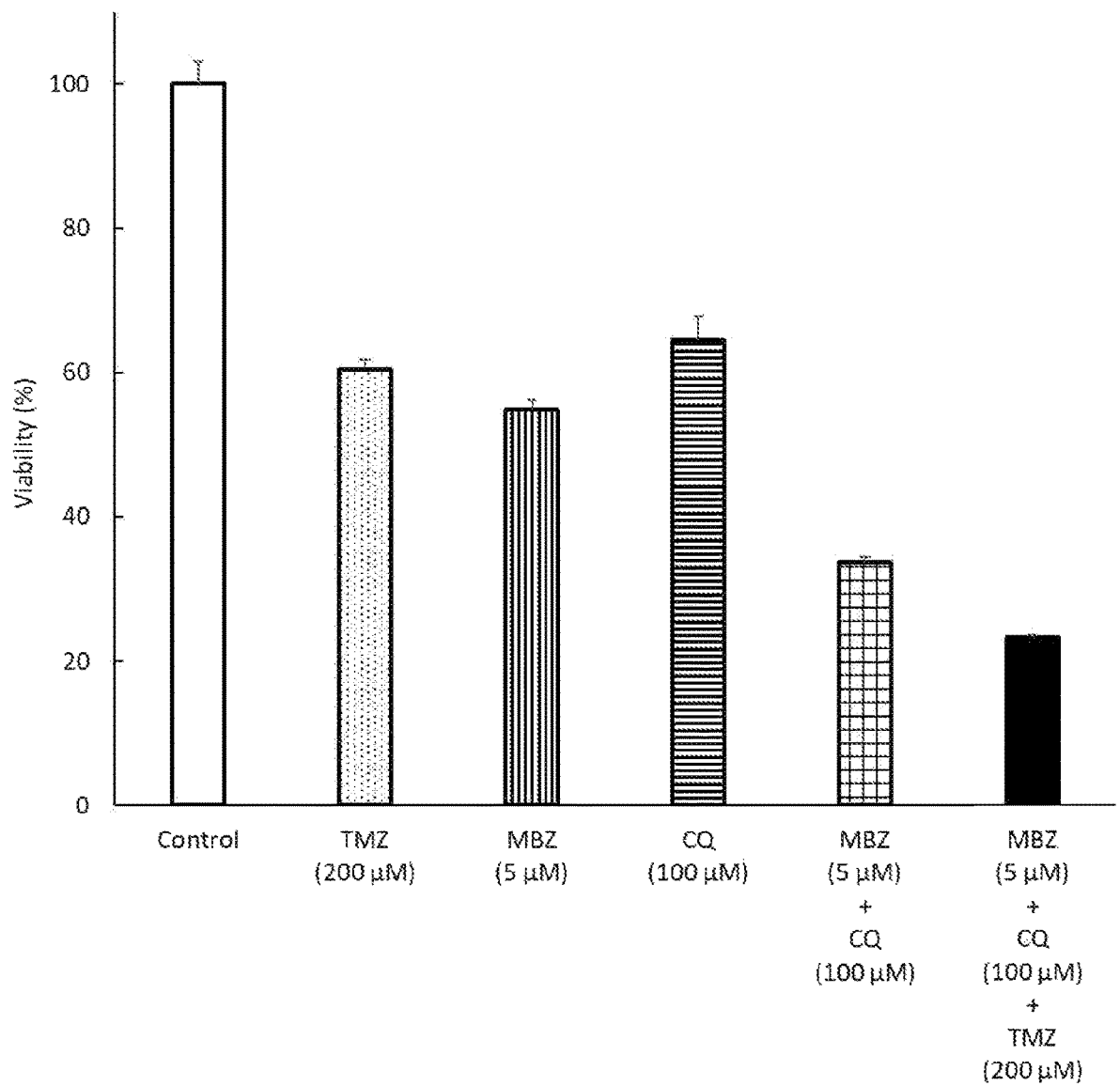
FIGS. 8A and 8B are bar graphs depicting the cell viability of glioblastoma GBM8401 cells towards TMZ (200 or 400 µM), after the treatment of the present sensitizer, which comprised MBZ (5 µM) and CQ (100 µM), in accordance with one embodiment of the present disclsoure.
Figure 8B:
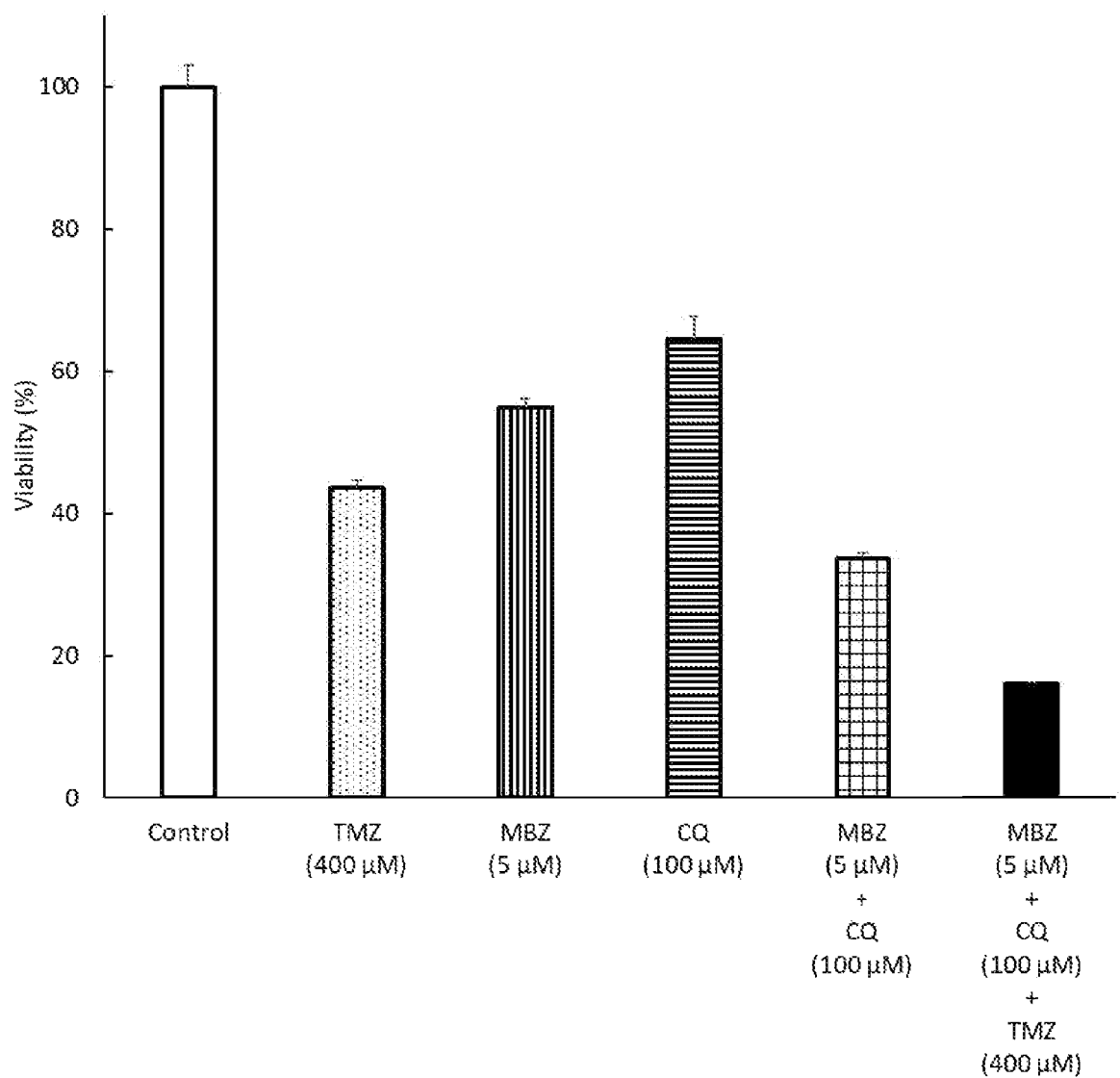

Reference is first made to FIG. 4, which depicts the cell viability of BxPC-3 cells towards the chemotherapeutic agent—gemcitabine (0.05 μM), after the treatment of the present sensitizer, which comprised MBZ (5 μM) and CQ (100 μM). It was found that when BxPC-3 cells were treated with a combination of MBZ (5 μM) and CQ (100 μM), cell viability dropped to about 38%. Surprisingly, when BxPC-3 cells were simultaneously treated with MBZ (5 µM), CQ (100 µM), and gemcitabine (0.05 µM), cell viability was further reduced, as compared to that of the combined treatment of MBZ and CQ, or the treatment of gemcitabine alone (FIG. 4). In other words, the present sensitizer (i.e., MBZ and CQ) enhanced the susceptibility of pancreatic cancer cells toward the chemotherapeutic agent—gemcitabine. Similar results were also found in drug resistant pancreatic cancer Mia-Paca-2/R cells (FIG. 5), hepatoma Sk-Hep-1 cells (FIGS. 6 and 7), and glioblastoma GBM8401 cells (FIGS. 8A and 8B), in which each cancer cell line became more susceptible to the treatment of the anti-cancer agent (e.g., doxorubicin, sorafenib, or TMZ).

2.2 Combined Treatment of MBZ, CQ and 4-PB on Drug Resistant Cancer Cells

Figure 9:
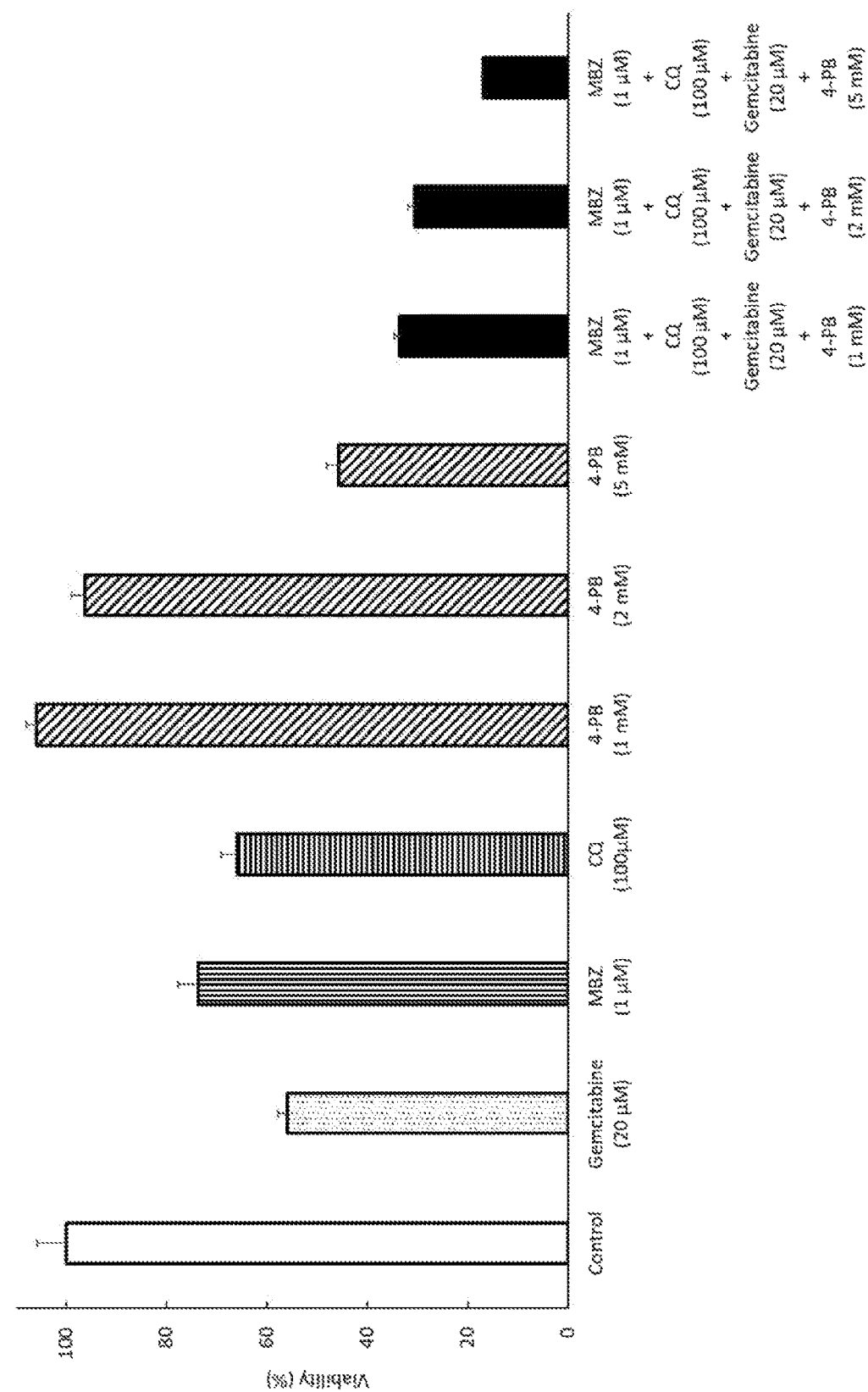
FIG. 9 is a bar graph depicting the effect of MBZ, CQ and 4-PB on the susceptibility of drug-resistant Panc-1/R cells toward gemcitabine in accordance with one embodiment of the present disclsoure.

Similar to the procedures described in Example 2.1, in this example, the treatment of MBZ, CQ and 4-PB on gencitabine resistant pancreatic cancer cells (Panc-1/Gem cells) was investigated. Results are illustrated in FIG. 9.

It was found that the combination of 4-PB (1 or 2 mM), MBZ (1 µM) and CQ (100 µM) was capable of reducing the viability of Panc-1/Gem cells to a level of about 35%. However, if the concentration of 4-PB in the present combo (i.e., the combination of MBZ, 4-PB and CQ) was increased to 5 mM, the viability of Panc-1/Gem cells would dropped to a low level of less than 20%.

The finding of this example is a clear indication that the combo treatment of the present sensitizer (i.e., at least two agents selected from the group consisting of an anti-parasitic agent, an autophagy inhibitor, and an HDAC inhibitor) may increase the susceptibility of drug resistant cancer cells toward the chemotherapeutic agent (e.g., gemcitabine), which the cancer cells had become resistant thereto.

Figure 10:
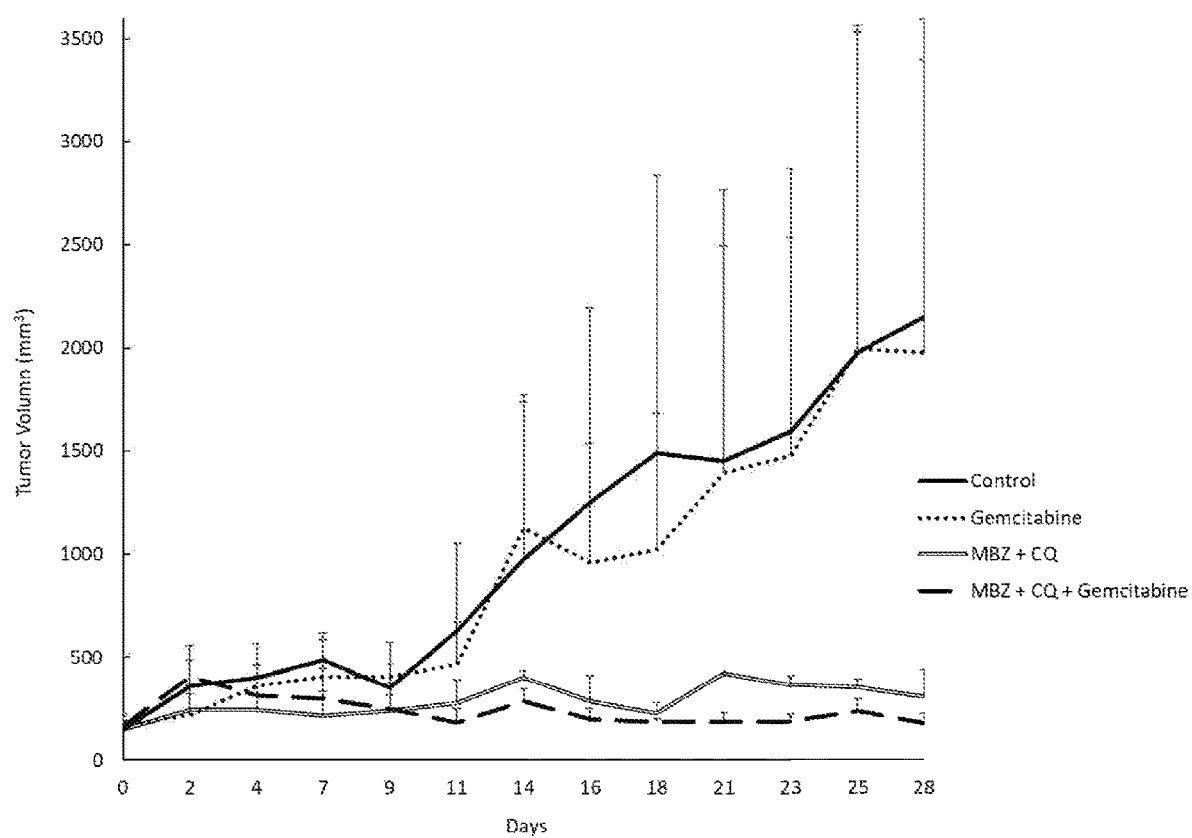
FIG. 10 is a line graph depicting the change in tumor volume in drug resistant pancreatic cancer xenograft mice independently treated with gemcitabine, the combo of MBZ and CQ, and the combo of gemcitabine, MBZ and CQ in accordance with one embodiment of the present disclsoure.
Figure 11:
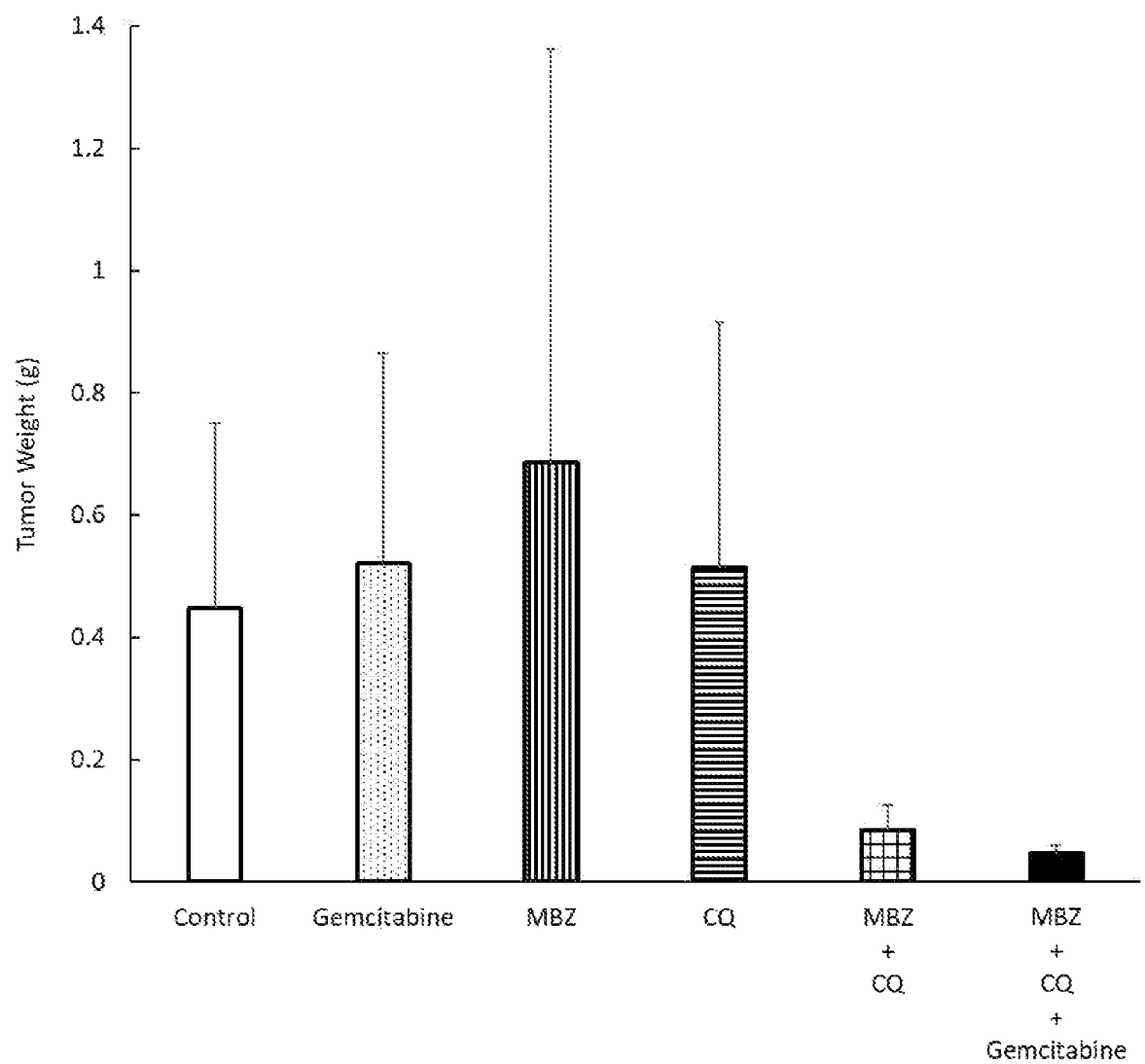
FIG. 11 is a bar graph depicting the change in tumor weight in drug resistant pancreatic cancer xenograft mice of FIG. 10.

Example 3 the Present Sensitizer Increases Susceptibility of Drug Resistant Cancer Cells Toward an Anti-Cancer Agent in Xenograft Pancreatic Cancer Mice Model Effects of the sensitizer of this disclosure on mice grafted with drug resistant pancreatic cancer Mia-Paca-2/R cells were investigated by measuring the grafted tumor volume and tumor weight in accordance with steps described in "Materials and Methods" section. Results are illustrated in FIGS. 10 and 11.

As depicted, treatment of MBZ and CQ, at the concentration of 100 mg/Kg/dose, for at least 12 doses (3 does/week, 4 weeks) was effective in reducing both the volume and the weight of the xenografted pancreatic tumor significantly, as compared with that of the control mice (i.e., mice that were injected with vehicle or gemcitabine only). Most significantly, both the volume and the weight of the xenografted tumor were further reduced when mice were exposed to MBZ, CQ and gemcitabine. In other words, the xenografted drug resistant pancreatic tumor became sensitive to gemcitabine after being exposed to the present sensitizer—MBZ and CQ.

Accordingly, the result of this disclosure confirmed that the present combo treatment (i.e., an anti-parasitic agent and an autophagy inhibitor, and optionally, an HDAC inhibitor) may be used to treat cancers, including drug resistant cancers; accordingly, the present combo treatment offers cancer patients that are non-responsive to the treatment of a chemotherapeutic agent a way to reverse the insensitivity of the cancer cells toward the chemotherapeutic agent, so that the growth of the cancer cells may be suppressed or inhibited.

The foregoing description of various embodiments of the disclosure has been presented for purpose of illustration and description. It is not intended to be exhaustive or to limit the disclosure to the precise embodiments disclosed. Numerous modifications or variations are possible in light of the above teachings. The embodiments discussed were chosen and described to provide the best illustration of the principles of the disclosure and its practical application to thereby enable one of ordinary skill in the art to utilize the disclosure in various embodiments and with various modifications as are suited to the particular use contemplated. All such modifications and variations are within the scope of the disclosure as determined by the appended claims when interpreted in accordance with the breadth to which they are fairly, legally, and equitably entitled.

What is claimed is:

1. A method for treating a cancer resistant to an anti-cancer agent in a subject, comprising administering to the subject an effective amount of an anti-parasitic agent and an autophagy inhibitor, wherein,
   the cancer is resistant to gemcitabine;
   the anti-parasitic agent is mebendazole (MBZ); and
   the autophagy inhibitor is chloroquine (CQ):
   wherein the cancer is brain tumor, liver cancer, or pancreatic cancer.

2. The method of claim 1, further comprising administering a histone deacetylase (HDAC) inhibitor before, together with, or after the anti-parasitic agent and the autophagy inhibitor are administered to the subject.

3. The method of claim 2, wherein the HDAC inhibitor is selected from the group consisting of belinostat, 4-phenylbutyrate (4-PB), romidepsin, and vorinostat.

4. The method of claim 1, wherein the cancer is the gemcitabine resistant liver cancer, the anti-parasitic agent is MBZ, and the autophagy inhibitor is CQ.

5. The method of claim 1, wherein the cancer is the gemcitabine resistant brain tumor, the anti-parasitic agent is MBZ, and the autophagy inhibitor is CQ.

6. The method of claim 3, wherein the cancer is the gemcitabine resistant pancreatic cancer, the anti-cancer agent is gemcitabine, the anti-parasitic agent is MBZ, the autophagy inhibitor is CQ, and the HDAC inhibitor is 4-PB.

* * * * *